US012564732B2

(12) United States Patent
Yang et al.

(10) Patent No.: US 12,564,732 B2
(45) Date of Patent: Mar. 3, 2026

(54) TUMOR RADIOTHERAPY PLANNING DESIGN METHOD AND APPARATUS, ELECTRONIC DEVICE AND STORAGE MEDIUM

(71) Applicant: Xiangya Hospital Central South University, Changsha (CN)

(72) Inventors: Xiaoyu Yang, Changsha (CN); Yuqian Zhao, Changsha (CN); Zhen Yang, Changsha (CN); Rui Wei, Changsha (CN); Ying Cao, Changsha (CN); Shuzhou Li, Changsha (CN); Qigang Shao, Changsha (CN); Du Tang, Changsha (CN); Zhao Peng, Changsha (CN)

(73) Assignee: Xiangya Hospital Central South University, Changsha (CN)

( * ) Notice: Subject to any disclaimer, the term of this patent is extended or adjusted under 35 U.S.C. 154(b) by 335 days.

(21) Appl. No.: 18/354,621

(22) Filed: Jul. 18, 2023

(65) Prior Publication Data

US 2024/0157171 A1 May 16, 2024

Related U.S. Application Data

(63) Continuation of application No. PCT/CN2023/087510, filed on Apr. 11, 2023.

(51) Int. Cl.
*A61N 5/10* (2006.01)
*G16H 20/40* (2018.01)
*G16H 50/20* (2018.01)

(52) U.S. Cl.
CPC ......... *A61N 5/1031* (2013.01); *A61N 5/1045* (2013.01); *G16H 20/40* (2018.01); *G16H 50/20* (2018.01)

(58) Field of Classification Search
CPC .... A61N 5/1031; A61N 5/1045; G16H 20/40; G16H 50/20
See application file for complete search history.

(56) References Cited

U.S. PATENT DOCUMENTS 11,011,264 B2 * 5/2021 Zankowski ............ G16H 50/20
11,020,615 B2 * 6/2021 Eriksson .............. A61N 5/1031
(Continued)

*Primary Examiner* — Sean M Luck

(57) ABSTRACT

A tumor radiotherapy planning design method and apparatus, an electronic device, and a computer storage medium are provided, including: obtaining a current optimization parameter vector set, and calculating a current cost function value; randomly correcting the current optimization parameter vector set to generate alternative optimization parameter vector sets; then performing planning parameter optimization, and calculating corresponding total cost function values; determining current optimal or suboptimal alternative optimization parameter vector sets according to the total cost function values, sampling to update the current optimization parameter vector set and the current cost function value according to the total cost function values of the current alternative optimization parameter vector sets, and then performing an iteration repeatedly until a convergence condition is satisfied; and outputting an optimal optimization parameter vector set after the iteration, determining planning parameters, and calculating and outputting planning MLC leaf positions and dose distributions.

14 Claims, 4 Drawing Sheets

(56)  References Cited

U.S. PATENT DOCUMENTS

| | | | | |
|---|---|---|---|---|
| 11,167,152 | B2 * | 11/2021 | Liu | A61N 5/103 |
| 2005/0143965 | A1 * | 6/2005 | Failla | G01T 1/02 |
| | | | | 703/2 |
| 2006/0145088 | A1 * | 7/2006 | Ma | H05H 15/00 |
| | | | | 250/396 ML |
| 2011/0153547 | A1 * | 6/2011 | McNutt | G06N 5/02 |
| | | | | 706/54 |
| 2014/0350863 | A1 * | 11/2014 | Hartman | A61N 5/1031 |
| | | | | 702/19 |
| 2015/0095043 | A1 * | 4/2015 | Cordero Marcos | G16H 20/40 |
| | | | | 705/2 |
| 2015/0352374 | A1 * | 12/2015 | Gattiker | A61N 5/1031 |
| | | | | 703/2 |
| 2016/0129282 | A1 * | 5/2016 | Yin | G16H 40/20 |
| | | | | 600/1 |
| 2016/0140300 | A1 * | 5/2016 | Purdie | G16H 20/40 |
| | | | | 705/2 |
| 2017/0004267 | A1 * | 1/2017 | Svatos | G16H 20/40 |
| 2017/0177812 | A1 * | 6/2017 | Sjölund | G16H 20/40 |
| 2017/0304651 | A1 * | 10/2017 | Takayanagi | A61N 5/1043 |
| 2018/0063386 | A1 * | 3/2018 | Sharma | H04N 23/60 |
| 2018/0304097 | A1 * | 10/2018 | Bokrantz | G06F 16/90335 |
| 2019/0030370 | A1 * | 1/2019 | Hibbard | A61N 5/1067 |
| 2019/0192880 | A1 * | 6/2019 | Hibbard | G16H 30/20 |
| 2019/0325620 | A1 * | 10/2019 | Adler | G06T 7/10 |
| 2019/0333623 | A1 * | 10/2019 | Hibbard | A61N 5/1039 |
| 2020/0043573 | A1 * | 2/2020 | Fält | G16B 50/00 |
| 2020/0188692 | A1 * | 6/2020 | Liu | A61N 5/1031 |
| 2020/0360728 | A1 * | 11/2020 | Tilly | A61N 5/1081 |
| 2021/0035340 | A1 * | 2/2021 | Wang | G16H 50/50 |
| 2021/0339046 | A1 * | 11/2021 | Lachaine | A61N 5/1037 |
| 2022/0054859 | A1 * | 2/2022 | Liu | G06N 20/00 |
| 2022/0088410 | A1 * | 3/2022 | Hibbard | A61N 5/1038 |

* cited by examiner

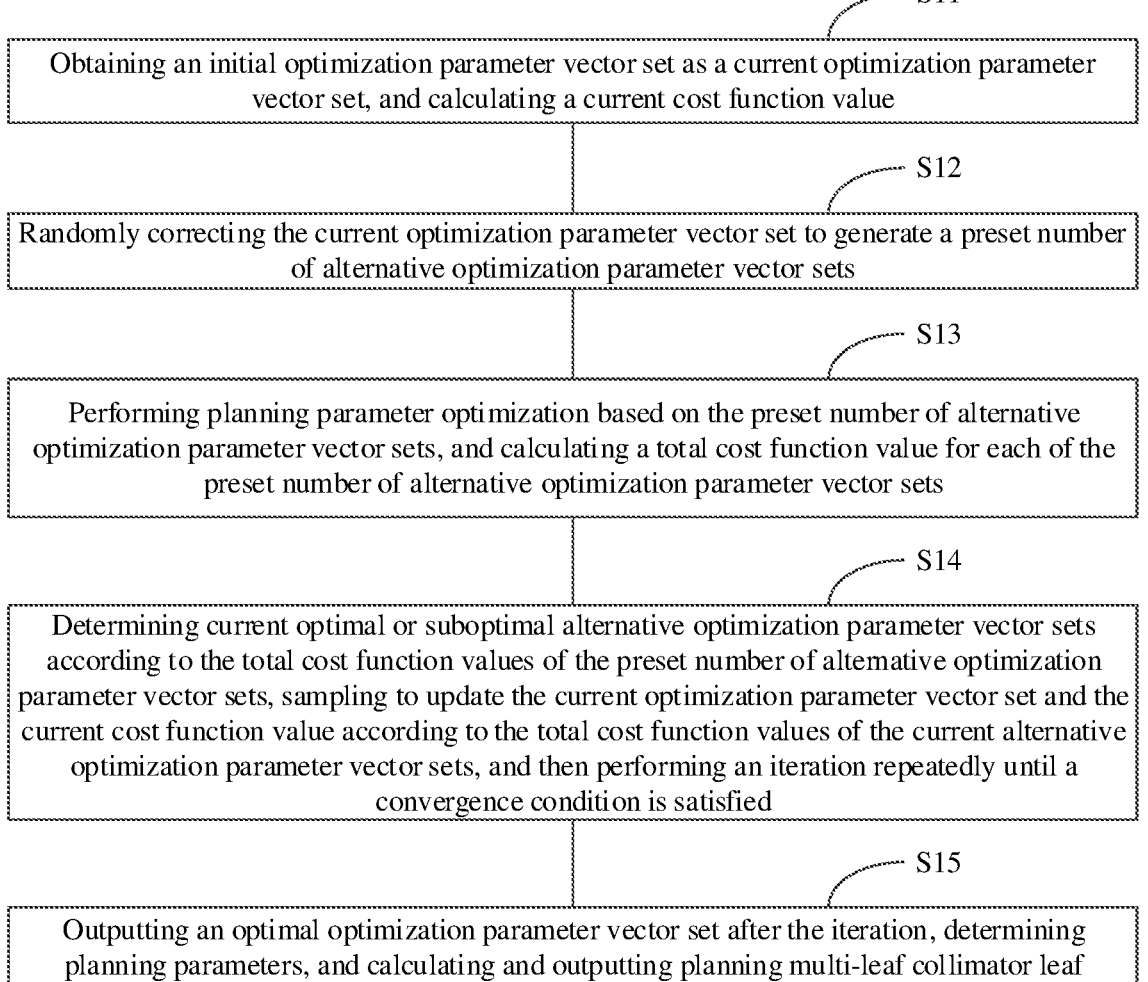

S11

Obtaining an initial optimization parameter vector set as a current optimization parameter vector set, and calculating a current cost function value

S12

Randomly correcting the current optimization parameter vector set to generate a preset number of alternative optimization parameter vector sets

S13

Performing planning parameter optimization based on the preset number of alternative optimization parameter vector sets, and calculating a total cost function value for each of the preset number of alternative optimization parameter vector sets

S14

Determining current optimal or suboptimal alternative optimization parameter vector sets according to the total cost function values of the preset number of alternative optimization parameter vector sets, sampling to update the current optimization parameter vector set and the current cost function value according to the total cost function values of the current alternative optimization parameter vector sets, and then performing an iteration repeatedly until a convergence condition is satisfied

S15

Outputting an optimal optimization parameter vector set after the iteration, determining planning parameters, and calculating and outputting planning multi-leaf collimator leaf positions and dose distributions

FIG. 1

9 Residual convolution modules

TUMOR RADIOTHERAPY PLANNING DESIGN METHOD AND APPARATUS, ELECTRONIC DEVICE AND STORAGE MEDIUM

TECHNICAL FIELD

The disclosure relates to the field of radiotherapy (also referred to radiation therapy) technology, particularly to a tumor radiotherapy planning design method and a tumor radiotherapy planning design apparatus, an electronic device, and a storage medium.

BACKGROUND

Intensity-modulated radiation therapy (abbreviated as IMRT) is a mainstream radiation therapy technology at present. The planning design is of great importance of the IMRT, including plan optimization and plan verification. In the phase of plan optimization, clinical staffs need to perform trial and error according to their own experience, and continuously adjust planning optimization parameters until dosimetric indicators of targets and organs at risk (OAR) meet corresponding requirements and reach optimal states considered by the staffs. In the phase of plan verification, the clinical staffs use a dose measurement device to verify plan delivery accuracy. Specially, the plan delivery accuracy is quantified by the gamma passing rates (GPR). If the plan delivery accuracy does not reach a preset standard, the plan needs to be redesigned until both the dosimetric indicators and the plan delivery accuracy reach the preset standard, and then the patient can be treated. However, trial and error of the planning optimization parameters and plan redesigning caused by failure of the plan verification result in heavy clinical workload. Therefore, it is of great importance to realize an automatic planning design with high quality and high delivery accuracy to improve clinical efficiency and reduce treatment waiting time of the patient. Furthermore, the automatic planning design is expected to improve patient treatment efficiency and is of great clinical significance.

At present, there are three automatic planning design methods, such as a knowledge-based planning (KBP) method, a protocol-based planning (PBP) method, and a multicriteria optimization-based planning (MCOP) method. The KBP method collects existed clinical treatment plans according to previous treatment cases to establish a database of specific tumor sites, trains an artificial intelligence model to learn a priori knowledge, predicts clinically achievable dosimetric indicators in view of the new patient, and then guides optimization parameters setting of the new planning design. The PBP method establishes a dosimetric optimization parameter template for the specific tumor sites based on the clinical experience, tightens optimization parameters of the organs at risk individually according to a preset script during the optimization upon hard constraint conditions until the process violates the hard constraint conditions and the doses to OARs cannot be further reduced, and then stops updating to determine the final optimization parameters. The MCOP method automatically generates a plan database based on initial dosimetric optimization conditions, which includes multiple Pareto optimal plans, and then the clinical staffs select the optimal plan that meets clinical requirements based on their clinical experience.

However, the existing automatic planning methods can only optimize dosimetric quantities (i.e., the dosimetric indicators of the targets and the organs at risk), which cannot optimize the plan delivery accuracy. The plan delivery accuracy can be determined only after being measured by the radiation detectors. Namely, the plan delivery accuracy is difficult to quantify during the phase of plan optimization, thereby hindering its optimization. Even if the plan delivery accuracy can be predicted during the phase of plan optimization, it is difficult to work out the gradient relationship between the plan delivery accuracy cost function and the planning parameters. A conventional fluence map optimization algorithm cannot achieve synchronous optimization of the dosimetric indicators and the delivery accuracy. If the plan delivery accuracy does not reach the preset standard, it is necessary to redesign the plan, which wastes time and manpower, delays the treatment of the patient. In addition, most of the existing automatic planning design methods depend on manual experience too much, leading to subjective errors and poor expansibility. For example, the KBP and PBP methods need to establish a corresponding plan database or a corresponding optimization parameter template according to the clinical experience through retrospective collection of clinical plans, quality of which determine the quality of the final automatic plans. If the collected plans' quality is poor, the quality of generated automatic plans will be worsened. Meanwhile, various tumor sites have various objective dosimetric indicators, different medical institutions have different treatment principles, and every planner has his or her own clinical experience and planning habits. Therefore, it is necessary to establish different databases or templates in view of different tumor sites, medical institutions, and planners to guarantee the automatic plan quality. It is too tedious and lack of extensibility. The MCOP method requires the planner to weight and choose a final plan among many Pareto optimal plans. Still, the plan quality depends on the planners' subjective experience.

SUMMARY

The disclosure provides a tumor radiotherapy planning design method and a tumor radiotherapy planning design apparatus, an electronic device, and a storage medium, to solve the problems that existing radiotherapy planning methods cannot simultaneously optimize dosimetric quantities and delivery accuracy and that existing automatic planning methods excessively depend on manual planning experience.

Based on the above object, an embodiment of the disclosure provides a tumor radiotherapy planning design method, including: obtaining an initial optimization parameter vector set as a current optimization parameter vector set, and calculating a current cost function value; randomly correcting the current optimization parameter vector set to generate a preset number of alternative optimization parameter vector sets; performing planning parameter optimization based on the preset number of alternative optimization parameter vector sets, and calculating a total cost function value for each of the preset number of alternative optimization parameter vector sets; determining current optimal or suboptimal alternative optimization parameter vector sets according to the total cost function values of the preset number of alternative optimization parameter vector sets, sampling to update the current optimization parameter vector set and the current cost function value according to the total cost function values, and then performing an iteration repeatedly until any convergence conditions are satisfied; and finally outputting an optimal optimization parameter vector set, determining planning parameters, and calculating and outputting planning multi-leaf collimator (MLC) positions and dose distributions.

In an embodiment, before the obtaining an initial optimization parameter vector set as a current optimization parameter vector set, and calculating a current cost function value, the method includes collecting planning parameters and corresponding gamma passing rate (GPR) data of a plurality of tumor sites and establishing a training data set; and training a GPR prediction model by using the training data set to obtain a trained GPR prediction model.

In an embodiment, the performing planning parameter optimization based on the preset number of the alternative optimization parameter vector sets, and calculating a total cost function value for each of the preset number of alternative optimization parameter vector sets, includes: performing the planning parameter optimization based on the preset number of alternative optimization parameter vector sets to obtain current planning parameters and current dosimetric indicators of each alternative optimization parameter vector set; and calculating their total cost function values according to the current planning parameters, the current dosimetric indicators, and objective dosimetric indicators by a multifunctional optimization total cost function.

In an embodiment, the performing the planning parameter optimization based on the preset number of alternative optimization parameter vector sets to obtain current planning parameters and current dosimetric indicators of each alternative optimization parameter vector set, includes: for each alternative optimization parameter vector set, determining beam angles or beam ranges based on computed tomography (CT) images and contoured structures; and performing the planning parameter optimization by a gradient-based optimization algorithm according to the beam angles to obtain the current planning parameters and the current dosimetric indicators. Furthermore, the current dosimetric indicators include: homogeneity indices of targets, conformity indices of the targets, and volume doses and average doses of organs at risk.

In an embodiment, the calculating the total cost function value for each alternative optimization parameter vector set according to the current planning parameters, the current dosimetric indicators, and objective dosimetric indicators by a multifunctional optimization total cost function, includes: for each alternative optimization parameter vector set, performing prediction by a trained GPR prediction model according to the current planning parameters to obtain a predicted GPR, and calculating a plan delivery accuracy cost function value by a plan delivery accuracy cost function according to the predicted GPR; calculating a plan dosimetric quality cost function value according to the current dosimetric indicators and the objective dosimetric indicators by a plan dosimetric quality cost function; and calculating the total cost function value by the multifunctional optimization total cost function according to the plan delivery accuracy cost function value and the plan dosimetric quality cost function value.

In an embodiment, the sampling to update the current optimization parameter vector set and the current cost function value according to the total cost function values of current alternative optimization parameter vector sets, and performing an iteration repeatedly until a convergence condition is satisfied, includes: performing a sampling decision to determine whether to adopt the current optimal or suboptimal alternative optimization parameter vector sets; and updating the current optimization parameter vector set and the current cost function value using the current optimal or suboptimal alternative optimization parameter vector sets and their total cost function values respectively, when the current optimal or suboptimal alternative optimization parameter vector sets are adopted; and determining whether the convergence condition is satisfied, which includes: times of the iteration reaching to a preset maximum iteration number, a time of the iteration reaching to a maximum iteration time, and a convergence of cost function value reduction; and returning the step of the randomly correcting the current optimization parameter vector set to generate a preset number of alternative optimization parameter vector sets, when the convergence condition is not satisfied.

In an embodiment, the performing a sampling decision to determine whether to adopt the current optimal or suboptimal alternative optimization parameter vector set, includes: calculating an acceptance probability of the current optimal or suboptimal alternative optimization parameter vector sets according to the total cost function values; and generating a random number between 0 and 1 based on a uniform distribution; adopting the current optimal or suboptimal alternative optimization parameter vector sets when the generated random number is less than the acceptance probability; or not adopting them when the random number is equal to or greater than the acceptance probability.

Based on the same concept, an embodiment of the disclosure further provides a tumor radiotherapy planning design apparatus, including: an initialization unit, an alternative set acquiring unit, a total cost calculating unit, an update iteration unit, and a planning output unit; in the embodiment of the disclosure, the initialization unit configured to obtain an initial optimization parameter vector set as a current optimization parameter vector set, and to calculate a current cost function value; the alternative set acquiring unit is configured to randomly correct the current optimization parameter vector set to generate a preset number of alternative optimization parameter vector sets; the total cost calculating unit is configured to perform planning parameter optimization based on the preset number of alternative optimization parameter vector sets, and to calculate a total cost function value of each of the preset number of alternative optimization parameter vector sets; the update iteration unit is configured to determine the optimal or suboptimal alternative optimization parameter vector sets according to the total cost function values of the preset number of alternative optimization parameter vector sets, to sample and update the current optimization parameter vector set and the current cost function value according to total cost function values of the current alternative optimization parameter vector sets, and to perform an iteration repeatedly until a convergence condition is satisfied; and the planning output unit is configured to output an optimal optimization parameter vector set after the iteration, determine planning parameters, and to calculate and output planning MLC positions and dose distributions. Each of the initialization unit, the alternative set acquiring unit, the total cost calculating unit, the update iteration unit, and the planning output unit is embodied by software stored in at least one memory and executable by at least one processor.

Based on the same concept, an embodiment of the disclosure further provides an electronic device, including: a memory, a processor, and a computer program stored on the memory and executable by the processor; and the processor is configured to implement the above-mentioned method when executing the computer program.

Based on the same concept, an embodiment of the disclosure further provides a non-transitory computer storage medium. In the embodiment of the disclosure, the non-transitory computer storage medium includes at least one executable instruction, and the executable instruction is configured to make a processor to execute the above-mentioned method.

Beneficial effects of the disclosure are as follows. As illustrated above, the embodiments of the disclosure provide a tumor radiotherapy planning design method and a tumor radiotherapy planning design method apparatus, an electronic device, and a storage medium. The method includes: obtaining an initial optimization parameter vector set as a current optimization parameter vector set, and calculating a current cost function value; randomly correcting the current optimization parameter vector set to generate a preset number of alternative optimization parameter vector sets; performing planning parameter optimization based on the preset number of alternative optimization parameter vector sets, and calculating a total cost function value of each of the preset number of alternative optimization parameter vector sets; determining the current optimal or suboptimal alternative optimization parameter vector sets according to the total cost function values of the preset number of alternative optimization parameter vector sets, sampling to update the current optimization parameter vector set and the current cost function value according to the total cost function values, and then performing an iteration repeatedly until a convergence condition is satisfied; and outputting an optimal optimization parameter vector set after the iteration, determining planning parameters, and calculating and outputting planning MLC positions and dose distributions, thereby simultaneously optimizing the radiotherapy planning dosimetric quality and the delivery accuracy, realizing automatic planning design with less reliance on manual experience, and saving clinical manpower and time costs.

BRIEF DESCRIPTION OF DRAWINGS

In order to illustrate embodiments of the disclosure or technical solutions in the related art, attached drawings that need to be used in the embodiments or the related art are briefly described below. Apparently, the attached drawings in the following description merely illustrate the embodiments of the disclosure, and those skilled in the related art may obtain other drawings according to the attached drawings without involving any creative effort.

FIG. 1 illustrates a schematic flowchart of a tumor radiotherapy planning design method according to an embodiment of the disclosure.

DETAILED DESCRIPTION OF EMBODIMENTS

In order to make the objectives, technical solutions, and advantages of the disclosure more clearly, the disclosure will be further described in detail below with reference to illustrated embodiments and with reference to attached drawings.

It should be noted that, unless otherwise defined, technical terms or scientific terminologies used in the embodiments of the disclosure belong to common meanings understood by those skilled in the related art. The terms "first", "second" and similar words used in the embodiments of the disclosure do not denote any order, quantity, or importance, but are merely used to distinguish different components. Words such as "comprising" or "including" are intended to indicate that elements or objects in front of the word encompass another elements or objects listed after the word and vice versa, without excluding other elements or objects. Descriptions such as "connected with" or "connected to" are not limited to physical or mechanical connections, but may include electrical connections, whether direct or indirect. The terms "upper", "lower", "left", "right" and the like are only used to represent a relative positional relationship, and when an absolute position of the described object is changed, the relative positional relationship may also be changed accordingly.

An embodiment of the disclosure provides a tumor radiotherapy planning design method, as shown in FIG. 1, the tumor radiotherapy planning design method includes the following steps.

Step 11, an initial optimization parameter vector set is obtained as a current optimization parameter vector set, and a current cost function value is calculated.

In the embodiment of the disclosure, vector coding is performed on initial optimization parameters to obtain the initial optimization parameter vector set which is used as the current optimization parameter vector set, and the current cost function value is calculated based on the current optimization parameter vector set. The initial optimization parameters include dose parameters, volume parameters, and weight parameters. The initial optimization parameter vector set includes dose optimization parameter vectors, volume optimization parameter vectors, and weight optimization parameter vectors. The dose optimization parameter vectors include dose optimization parameters for all serial organs, the volume optimization parameter vectors include volume optimization parameters for all parallel organs, and the weight optimization parameter vectors include weight optimization parameters of all targets and organs at risk (OAR).

Figure 2:
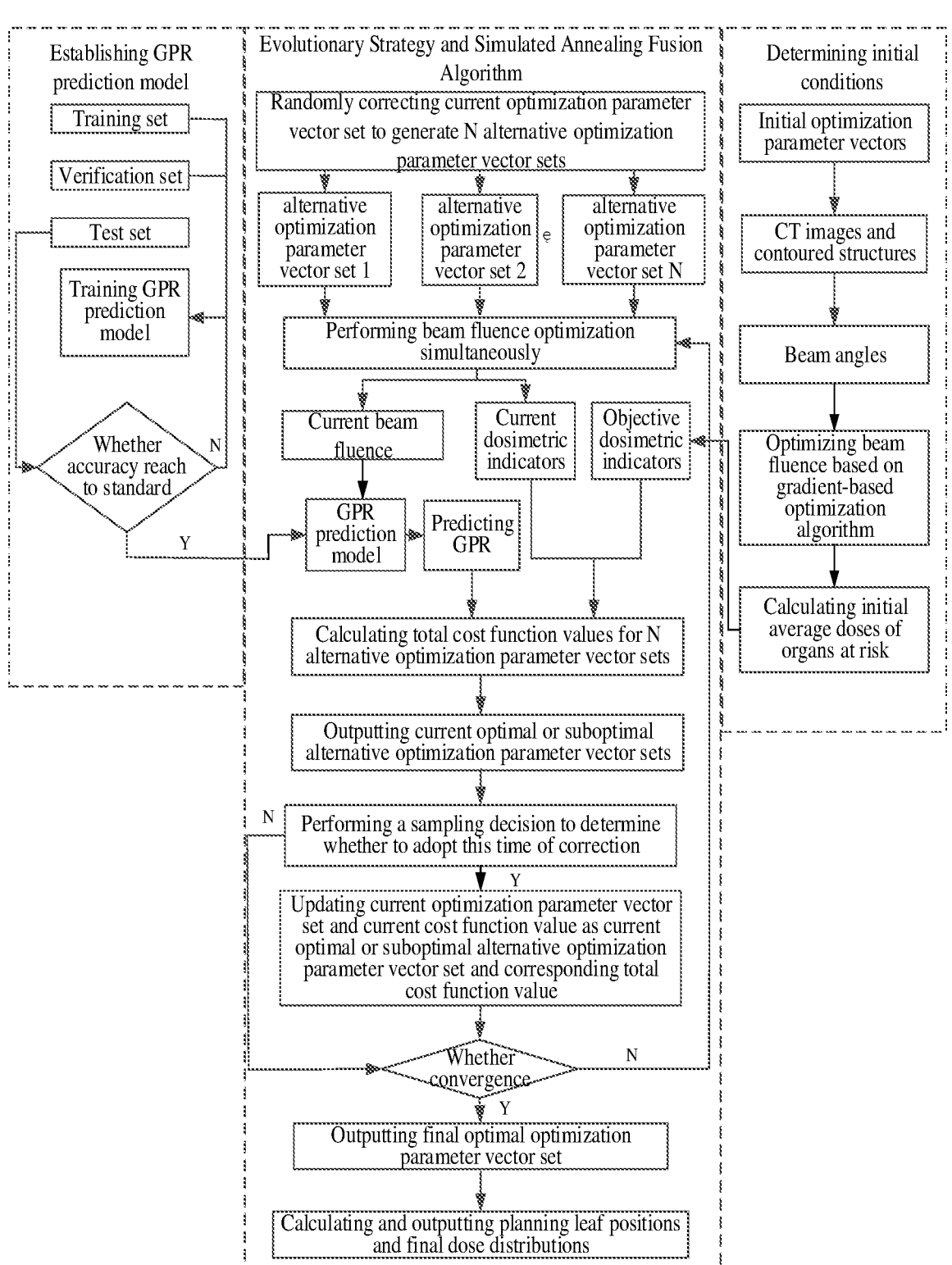
FIG. 2 illustrates a schematic detailed diagram of the tumor radiotherapy planning design method according to the embodiment of the disclosure.

In the embodiment of the disclosure, before the step S11, a Gamma passing rate (GPR) prediction model needs to be trained to obtain a trained GPR prediction model. In an illustrated embodiment, as shown in FIG. 2, planning parameters and corresponding GPR data of a plurality of tumor sites are collected, and a training data set is established; and then the GPR prediction model is trained based on the training data set to obtain the trained GPR prediction model. The planning parameters include beam fluence and aperture shapes. In the embodiment of the disclosure, the training data set is divided into a training set, a verification set, and a test set, the GPR prediction model is trained by using the training set and the verification set, and a prediction accuracy of the GPR prediction model is tested by using the test set. The planning parameters are used as an input of the GPR prediction model (i.e., beam fluence maps or the aperture shapes), and the GPR is used as an output of the GPR prediction model. The GPR prediction model can be a classical machine learning model, such as Poisson regression, AdaBoost algorithm, and a random forest model. Furthermore, the GPR prediction model can be a deep learning model, such as a convolutional neural network, a residual neural network, a transformer model, etc.

When the current cost function value is calculated based on the current optimization parameter vector set, firstly, single planning parameter optimization is performed on the current optimization parameter vector set by a gradient-based optimization algorithm to obtain current planning parameters and current dosimetric indicators which correspond to the current optimization parameter vector set. The trained GPR prediction model is applied to predict the GPR to obtain a predicted GPR. The predicted GPR is used to calculate a plan delivery accuracy cost function value. A plan dosimetric quality cost function value is calculated according to the dosimetric indicators, and then a multifunctional optimization total cost function value is further calculated corresponding to the current optimization parameter vector and set as the current cost function value. The gradient-based optimization algorithm can be selected from a gradient descent algorithm, an interior point optimization or Newton method, etc. which is not limited herein.

In the embodiment of the disclosure, with continued reference to FIG. 2, computed tomography (CT) images and structures are obtained, and then beam angles or ranges are obtained. The planning parameters are optimized based on the gradient-based optimization algorithm, and initial average doses $\bar{d}_{OAR}^{(int)}$ of the organs at risk are calculated to obtain objective dosimetric indicators.

The plan delivery accuracy cost function is expressed as follows:

$$\mathcal{L}_{acc} = \min\left(1, \max\left(\frac{GPR^+ - \overline{GPR}}{GPR^+ - GPR^-}, 0\right)\right), \quad (1);$$

and $$\overline{GPR} = 1/N_f \cdot \sum_{i=1}^{N_f} GPR_i, \quad (2).$$

In the above formulas, $\mathcal{L}_{acc}$ represents the plan delivery accuracy cost function, $\overline{GPR}$ represents an average value of the predicted GPRs, which is calculated by the formula (2), $GPR_+$ and $GPR_-$ respectively represent an upper limit and a lower limit of a preset GPR. In an illustrated embodiment, the $GPR_+$ and $GPR_-$ are 1.00 and 0.85, respectively. Furthermore, in the formula (2), $N_f$ represents a number of planning beams, and $GPR_i$ represents an ith beam GPR predicted by the trained artificial intelligence model (i.e., the trained GPR prediction model).

The plan dosimetric quality cost function is expressed as follows:

$$\mathcal{L}_{qlt} = \frac{\sum_{j=1}^{N_D} \left(2^{-t_j+1} \cdot \mathcal{D}_j\right)}{\sum_{j=1}^{N_D} 2^{-t_j+1}}.$$

In the formula, $\mathcal{L}_{qlt}$ represents the plan dosimetric quality cost function, $N_D$ represents a number of the dosimetric indicators to be evaluated, $t_j$ represents a weight coefficient parameter of a jth dosimetric indicator, $D_j$ includes homogeneity indices $D_{HI}$ of the targets, conformity indices $D_{CI}$ of the targets, and dose indicators $D_{OAR}$ of the organs at risk, which are respectively expressed as follows:

$$\mathcal{D}_{HI} = \min\left(1, \max\left(\frac{HI - HI^-}{HI^+ - HI^-}, 0\right)\right);$$

-continued $$\mathcal{D}_{CI} = \min\left(1, \max\left(\frac{CI^+ - CI}{CI^+ - CI^-}, 0\right)\right); \text{ and}$$

$$\mathcal{D}_{OAR} = \min\left(1, \max\left(\frac{\bar{d}_{OAR} - \bar{d}_{OAR}^-}{\bar{d}_{OAR}^+ - \bar{d}_{OAR}^-}, 0\right)\right).$$

In the above formulas, HI represents a homogeneity index value of a target, and $HI^+$ and $HI^-$ represent preset upper and lower limits of the homogeneity index value of the target, respectively. In an illustrated embodiment, the $HI^+$ and the $HI^-$ are 8.0 and 3.0, respectively. CI represents a conformity index value of the target, $CI^+$ and $CI^-$ represent preset upper and lower limits of the conformity index value of the target, respectively. In an illustrated embodiment, the $CI^+$ and the $CI^-$ are 0.95 and 0.65, respectively. Furthermore, in the formulas, $\bar{d}_{OAR}$ represents an average dose of a certain organ at risk, and $\bar{d}_{OAR}^+$ and $\bar{d}_{OAR}^-$ represent a preset upper limit and a preset lower limit corresponding to the average dose of the certain organ at risk, respectively. The objective dosimetric indicators include, but are not limited to, upper and lower limits of the homogeneity index value HI of the target, upper and lower limits of the conformity index value CI of the target, upper and lower limits of the average dose of the certain organ at risk, etc. In an illustrated embodiment, the upper and the lower limits of the average doses of the organs at risk can be 1.1 times and 0.9 times of the initial average doses $\bar{d}_{OAR}^{(int)}$, respectively. In an illustrated embodiment, the HI and the CI can be expressed as follows:

$$HI = \frac{D_5 - D_{95}}{D_p} \times 100; \text{ and}$$

$$CI = \frac{(TV_{95})^2}{TV \times V_{95}}.$$

In the above formulas, $D_5$ and $D_{95}$ represent maximum doses achieved at 5% and 95% of the target, respectively, $D_p$ represents a prescription dose corresponding to the target, $TV_{95}$ represents a volume within the target that reaches 95% of the prescription dose, TV represents a volume of the target, $V_{95}$ represents a volume that reaches 95% of the prescription dose, including inside and outside of the target.

The multifunctional optimization total cost function $\mathcal{L}_{tot}$ is obtained using a weighted summation method in combination with the plan delivery accuracy cost function and the plan dosimetric quality cost function, which is expressed as follows:

$$\mathcal{L}_{tot} = \lambda \cdot \mathcal{L}_{acc} + \mathcal{L}_{qlt}.$$

In the above formula, $\lambda$ represents a relative weight factor between the plan delivery accuracy cost function and the plan dosimetric quality cost function. In an illustrated embodiment, the $\lambda$ is in a range of 10.0 to 30.0.

Step S12, the current optimization parameter vector set are randomly corrected to generate a preset number of alternative optimization parameter vector sets.

In the step S12, as shown in FIG. 2, the current optimization parameter vector set is randomly corrected in each iteration, and a preset number N of alternative optimization parameter vector sets are generated. The random correction method can be selected from a random correction based on Gaussian distribution, or other random correction methods, such as uniform distribution, which is not limited herein. In an illustrated embodiment, N is in a range of 5 to 20. Various optimization parameter vectors are corrected according to the following formula:

$$\vec{p}'_{opt} = |\vec{p}_{opt} + \alpha \cdot \vec{r}_n \cdot \vec{p}_{opt}|.$$

In the formula, $\vec{p}'_{opt}$ represents a generated dose alternative optimization parameter vector, or a generated volume alternative optimization parameter vector, or a generated weight alternative optimization parameter vector; $\vec{p}_{opt}$ represents a current dose optimization parameter vector, or a current volume optimization parameter vector, or a current weight optimization parameter vector; $\vec{r}_n$ represents a random number vector generated on the basis of standard normal distribution, a number of elements of which is consistent with that of the $\vec{p}_{opt}$; and $\alpha$ represents a correction rate. In an illustrated embodiment, when the dose optimization parameter vector and the volume optimization parameter vector are corrected, $\alpha$ is about 0.05. In addition, different optimization parameter vectors can select the same or different $\alpha$ values. Meanwhile, when the weight optimization parameter vector is corrected, $\alpha$ is about 0.20, and different weight optimization parameter vectors can select the same or different $\alpha$ values.

Step S13, planning parameter optimization is performed based on the preset number of alternative optimization parameter vector sets simultaneously and a total cost function value for each of the preset number of alternative optimization parameter vector sets is calculated.

In the step S13, with continued reference to FIG. 2, firstly, the planning parameter optimization is performed based on the preset number of alternative optimization parameter vector sets simultaneously to obtain the current planning parameters and the current dosimetric indicators of each alternative optimization parameter vector set. In an illustrated embodiment, for each alternative optimization parameter vector set, the beam angles or ranges are determined based on the CT images and the structures; and the planning parameter optimization is performed by the gradient-based optimization algorithm according to the beam angle to obtain the current planning parameters and the current dosimetric indicators. Furthermore, the current dosimetric indicators include: the homogeneity indices of the targets, the conformity indices of the targets, and the volume doses and the average doses of the organs at risk.

Then, the total cost function value for each alternative optimization parameter vector set is calculated according to the current planning parameters, the current dosimetric indicators, and the objective dosimetric indicators by the multifunctional optimization total cost function. In an illustrated embodiment, for each alternative optimization parameter vector set, the prediction is performed by the trained GPR prediction model according to the current planning parameters to obtain a predicted GPR, and the plan delivery accuracy cost function value is calculated according to the predicted GPR; the plan dosimetric quality cost function value is calculated according to the current dosimetric indicators and the objective dosimetric indicators by the plan dosimetric quality cost function; and the total cost function value is calculated by the multifunctional optimization total cost function according to the plan delivery accuracy cost function value and the plan dosimetric quality cost function value. The calculation method of the total cost function value in this step is the same as that of the step S11, and details are not described herein again.

Step S14, a current optimal alternative optimization parameter vector set and several current suboptimal alternative optimization parameter vector sets (also referred to current alternative optimization parameter vector sets together) are determined according to the total cost function values of the preset number of alternative optimization parameter vector sets, the current optimization parameter vector set and the current cost function value are updated via sampling according to the total cost function values of the current alternative optimization parameter vector sets, and then an iteration is performed repeatedly until a convergence condition is satisfied.

In the embodiment of the disclosure, the current alternative optimization parameter vector sets with the lowest or sub-lowest total cost function values are selected from the preset number N of the alternative optimization parameter vector sets, and then are determined as the current optimal or suboptimal alternative optimization parameter vector sets.

With continued reference to FIG. 2, when the current optimization parameter vector set and the current cost function value are sampled to update, a sampling decision is performed to determine whether to adopt the current optimal or suboptimal alternative optimization parameter vector set. If adopted, the current optimal or suboptimal alternative optimization parameter vector set and the corresponding total cost function value will be respectively updated as the current optimization parameter vector set and the current cost function value. Then, it is determined whether the convergence conditions are satisfied, where the convergence conditions can be times of the iteration reaching to a preset maximum iteration number, or a time of the iteration reaching to a maximum iteration time, or a convergence of cost function value reduction. If the current optimal or suboptimal alternative optimization parameter vector set is not adopted, it will be directly determined whether the convergence conditions are satisfied. And then, if none of the convergence conditions are satisfied, the planning design method will return to the step S12 to begin the next iteration. If any of the convergence conditions are met, the iteration will terminate.

In the step S14, when the sampling decision is performed to determine whether to adopt the current optimal or suboptimal alternative optimization parameter vector set, an acceptance probability $p(\mathcal{L}_{tot}, \mathcal{L}'_{tot})$ is first calculated according to the total cost function values. And the acceptance probability $p(\mathcal{L}_{tot}, \mathcal{L}'_{tot})$ is calculated by the following formula:

$$p(\mathcal{L}_{tot}, \mathcal{L}'_{tot}) = \begin{cases} 1.0, & \mathcal{L}'_{tot} \leq \mathcal{L}_{tot} \\ \exp\left(\dfrac{\mathcal{L}_{tot} - \mathcal{L}'_{tot}}{\beta \cdot \exp(-\gamma \cdot k)}\right), & \mathcal{L}'_{tot} > \mathcal{L}_{tot} \end{cases}.$$

In the formula, $\mathcal{L}'_{tot}$ and $\mathcal{L}_{tot}$ represent the total cost function value of the current optimal or suboptimal alternative optimization parameter vector set and the current cost function value, respectively, $\beta$ represents an initial temperature parameter, and in an illustrated embodiment, $\beta$ is in a range of 0.01 to 0.10, $\gamma$ represents an attenuation factor parameter, and in an illustrated embodiment, $\gamma$ is in a range of 0.01 to 0.10, and k represents times of the iteration for the planning optimization.

And then, a random number between 0 and 1 is randomly generated based on a uniform distribution; if the random number is less than the calculated acceptance probability, the current optimal or suboptimal alternative optimization parameter vector set will be adopted; otherwise, not adopted.

In the related art, a manual trial and error process is as follows: performing planning parameter optimization based on preset optimization parameters and calculating the corresponding dosimetric indicators after this optimization; determining whether dosimetric indicators of targets and organs at risk reach clinical requirements, and whether the obtained treatment plan can be improved; manually modifying the planning optimization parameters by the designer according to his or her manual experience when the treatment plan does not meet the clinical requirements or can be improved; repeatedly performing the above manual parameter modification until the treatment plan reaches the clinical requirements and the optimal state considered by the designer, then finishing the manual trial and error, and outputting the corresponding treatment plan. The manual trial and error process is too time-consuming in the clinical planning optimization and its quality seriously depends on the designer's experience.

According to the embodiment of the disclosure, the manual planning trial and error are simulated based on the meta-heuristic algorithms, the planning optimization parameters are automatically adjusted, thereby realizing the automatic radiotherapy planning design. For example, from the steps S12 to S14, an evolutionary strategy and a simulated annealing fusion algorithm are applied to simulate the manual planning trial and error, which is less dependent on manual planning design experience, has little subjective error and high automation degree. In addition, there is no need to establish a plan database or an optimization template in view of a specific medical institution, a specific disease, and a specific designer, which saves manpower and time costs, is easy to popularize, and reduces the patients' treatment waiting time.

Step S15, an optimal optimization parameter vector set is output after the iteration, planning parameters are determined, and planning multi-leaf collimator (MLC) leaf positions and dose distributions are calculated and output.

In the embodiment of the disclosure, if the convergence conditions are satisfied, the iteration will terminate, thereby outputting the final optimal optimization parameter vector set after the iteration, determining the planning parameters, and calculating and outputting the planning MLC leaf positions and the dose distributions, that is, the final tumor radiotherapy plan is obtained. Meanwhile, the final optimal optimization parameter vector set after the iteration refers to the optimization parameter vector set with the minimum total cost function value during various times of the iteration.

In an embodiment of the disclosure, advantages of the proposed tumor radiotherapy planning design method are verified by comparing with the manual planning design method, including radiotherapy planning designs of seven brain tumor patients and seven lung cancer patients. Specially, 1541 pairs of beam fluence and corresponding GPRs at multiple planning sites are collected to form the data set. The data set is randomly divided into a training set, a verification set and a test set, the GRP prediction model is trained by using the training set and the verification set, the prediction accuracy of the model is tested by using the test set, and an average absolute error is 0.015.

Figure 3:
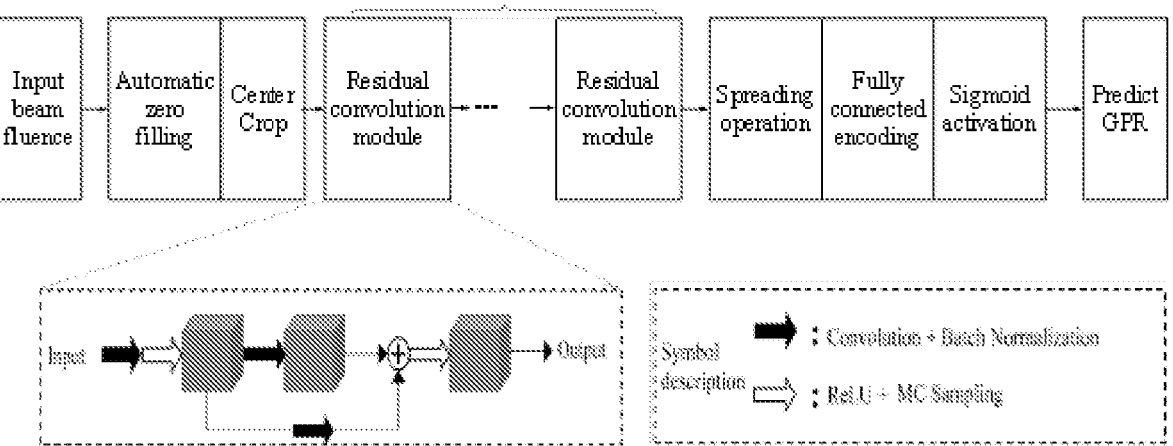
FIG. 3 illustrates a schematic structural diagram of a gamma passing rate (GPR) prediction model in the tumor radiotherapy planning design method according to an embodiment of the disclosure.

According to the tumor radiotherapy planning design method provided by the embodiment of the disclosure, the GPR prediction model adopts a deep learning model, a main body of which is a residual convolution network, and in an illustrated embodiment, a model structure is illustrated in FIG. 3. As shown in FIG. 3, MC Dropout represents Monte Carlo sampling (i.e., MC sampling), and the rectified linear units, abbreviated as ReLU, are used as neural activation functions. An input of the GPR prediction model is planning beam fluence maps, which passes through automatic zero filling (also referred to zero padding) and center crop standardization model input, and then is encoded by 9 residual convolution modules and 2 fully connected layers, and finally is activated by a Sigmoid function, thereby outputting the predicted GPR.

In order to ensure the accuracy and efficacy of the radiotherapy plan, before the patient is treated, a radiation detector array needs to be used to perform experimental measurement on the patient's radiotherapy plan delivery, and the GPR of the measurement result is analyzed. The GPR is determined by a difference between a radiotherapy planning dose and a measured dose, a value of the GPR is in a range of 0% to 100%, and the closer to 100% indicates that the higher the plan passing rate is, the better the delivery accuracy is. TG 218 report published by American Association of Physics in Medicine (AAPM) recommends using 90% GPR (with a calculation parameter of 3%/2 millimeters abbreviated as mm) as an intervention standard for whether the plan passes or not. Specially, GPR≥90% indicates that the plan passes verification and GPR<90% indicates that the plan is not passed.

TABLE 1

| Plan quality comparison table between manual planning and automatic planning | | |
| --- | --- | --- |
| Dosimetric indicators (unit) | Manual planning | Automatic planning based on multifunctional optimization |
| Homogeneity | 6.11 ± 2.16 | 3.51 ± 0.72 |
| Conformity | 0.85 ± 0.06 | 0.82 ± 0.09 |
| Brainstem maximum dose (gray abbreviated as Gy) | 42.76 ± 17.02 | 42.52 ± 19.69 |
| Left crystal maximum dose (Gy) | 3.84 ± 0.47 | 3.68 ± 0.84 |
| Right crystal maximum dose (Gy) | 4.66 ± 2.19 | 4.60 ± 1.24 |
| Maximum dose of optic chiasm (Gy) | 43.05 ± 21.89 | 42.88 ± 23.87 |
| Maximum dose of left optic nerve (Gy) | 20.32 ± 18.99 | 19.54 ± 19.12 |
| Maximum dose of right optic nerve (Gy) | 32.92 ± 25.85 | 28.10 ± 22.40 |
| Pituitary maximum dose (Gy) | 39.53 ± 20.98 | 34.63 ± 21.37 |
| Spinal cord maximum dose (Gy) | 38.00 ± 3.35 | 37.45 ± 6.35 |
| Mean dose to both lungs (Gy) | 8.51 ± 0.87 | 8.39 ± 0.98 |
| Mean cardiac dose (Gy) | 3.21 ± 3.17 | 2.89 ± 3.02 |
| Whole body average dose (Gy) | 6.96 ± 4.22 | 6.78 ± 3.98 |

Table 1 illustrates the plan quality comparison between the automatic planning by using the tumor radiotherapy planning design method provided by the embodiment of the disclosure and the manual planning. According to the comparison, the homogeneity index value of the target provided by the automatic planning in the embodiment of the disclosure is apparently superior to that of the manual planning, the conformity index value of the target is close to the manual planning, and the dosimetric indicators of the brainstem, the crystals, the optic nerves, the optic chiasm, the pituitary, the spinal cord, the lungs, the heart and the whole body are all superior to those of the manual planning.

TABLE 2

| | | |
|---|---|---|
| Delivery accuracy comparison between manual planning and automatic planning | | |
| Item | Manual planning | Automatic planning based on multifunctional optimization |
| Gamma passing rate (GPR, %) | 96.5 ± 4.8 | 97.0 ± 3.3 |
| Number of failed beams (GPR <90%) | 10 | 5 |

Table 2 illustrates a statistical comparison of plan delivery accuracy measurement results between the automatic planning provided by the tumor radiotherapy planning design method of the disclosure and the manual planning. According to the comparison results, the GPR of the multifunctional optimization-based automatic planning of the disclosure is slightly higher than that of the manual planning, and a measurement number of failed beams (i.e., regarding GPR<90% as failing to pass) of the automatic planning is significantly reduced in view of that of the manual planning.

According to the tumor radiotherapy planning design method provided by the embodiment of the disclosure, the multifunctional synchronous optimization capability is achieved; the GPR prediction model is brought into the planning optimization framework; the radiotherapy plan quality and the plan delivery accuracy can be synchronously optimized in combination with the meta-heuristic algorithms and the beam fluence optimization algorithms, which considers both of the plan quality and the plan delivery accuracy; a proportion of the plan verification failure is reduced; and the patient treatment efficiency of the patient is expected to be improved. Furthermore, the manual trial and error process of planning optimization is simulated by using an evolutionary strategy and a simulated annealing fusion algorithm, which less depends on manual planning design experience, and has less subjective errors and high automation degree. In addition, the planning design method of the disclosure has no need to establish a plan database or a plan optimization template in view of a specific medical institution, a specific disease, and a specific planner, which saves manpower and time costs, is easy to popularize, and reduces the patients' treatment waiting time.

The tumor radiotherapy planning design method provided by the embodiment of the disclosure includes the following steps: obtaining an initial optimization parameter vector set as a current optimization parameter vector set, and calculating a current cost function value; randomly correcting the current optimization parameter vector set to generate a preset number of alternative optimization parameter vector sets; performing planning parameter optimization based on the preset number of alternative optimization parameter vector sets simultaneously, and calculating a total cost function value for each of the preset number of alternative optimization parameter vector sets; determining current optimal or suboptimal alternative optimization parameter vector sets according to the total cost function values of the preset number of alternative optimization parameter vector sets, sampling to update the current optimization parameter vector set and the current cost function value according to the total cost function values, and then performing an iteration repeatedly until a convergence condition is satisfied; and outputting an optimal optimization parameter vector set after the iteration, determining planning parameters, and calculating and outputting planning MLC leaf positions and dose distributions. Therefore, the planning design method of the disclosure can simultaneously optimize the radiotherapy plan quality and the plan delivery accuracy, can realize the planning design automatically with less reliance on the manual experience, and can save clinical manpower and time costs.

The illustrated embodiments of the disclosure are described above. In some cases, the operations or steps recited in the embodiments of the disclosure may be performed in an order different from the order in the embodiments and may still achieve the desired results. In addition, the processes depicted in the attached drawings do not necessarily require a certain order shown or a sequential order to achieve the desired results. In some implementations, multi-task processing and parallel processing are also possible or may be advantageous.

Figure 4:
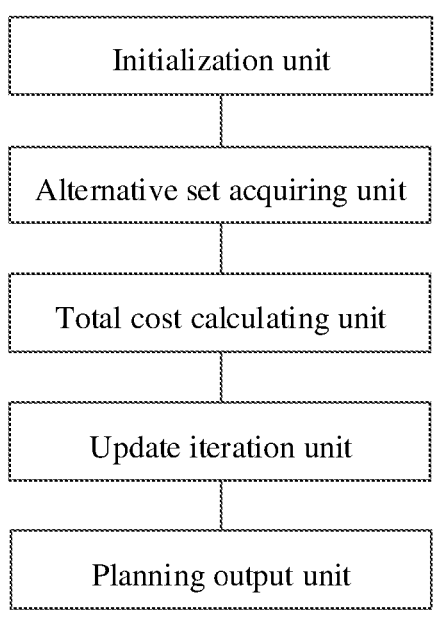
FIG. 4 illustrates a schematic structural diagram of a tumor radiotherapy planning design apparatus according to an embodiment of the disclosure.

Based on the same concept, an embodiment of the disclosure further provides a tumor radiotherapy planning design apparatus. As shown in FIG. 4, the tumor radiotherapy planning design apparatus includes: an initialization unit, an alternative set acquiring unit, a total cost calculating unit, an update iteration unit, and a planning output unit.

In an illustrated embodiment, the initialization unit is configured to obtain an initial optimization parameter vector set as a current optimization parameter vector set, and to calculate a current cost function value.

In an illustrated embodiment, the alternative set acquiring unit is configured to randomly correct the current optimization parameter vector set to generate a preset number of alternative optimization parameter vector sets.

In an illustrated embodiment, the total cost calculating unit is configured to perform planning parameter optimization based on the preset number of alternative optimization parameter vector sets, and to calculate a total cost function value for each of the preset number of alternative optimization parameter vector sets.

In an illustrated embodiment, the update iteration unit is configured to determine optimal or suboptimal alternative optimization parameter vector sets according to the total cost function values of the preset number of alternative optimization parameter vector sets, to sample to update the current optimization parameter vector set and the current cost function value according to the total cost function values, and to perform an iteration repeatedly until a convergence condition is satisfied.

In an illustrated embodiment, the planning output unit is configured to output an optimal optimization parameter vector set after the iteration, to determine planning parameters, and to calculate and output planning MLC leaf positions and dose distributions.

For convenience of description, the above-mentioned apparatus of the disclosure is divided into various units according to different functions of the various units, and then the various units are described one by one. However, it should be noted that the functions of each unit can be realized in a same or multiple software and/or hardware when the embodiments of the disclosure are implemented.

The apparatus according to the above embodiment is applied to implement the corresponding planning design method in the above-mentioned embodiment and has the beneficial effects corresponding to those of the planning design method. Therefore, details of the embodiment of the apparatus of the disclosure are not described herein again.

Based on the same concept, an embodiment of the disclosure further provides an electronic device, and the electronic device includes a memory, a processor, and a computer program stored on the memory and executable by the processor. Furthermore, the processor implements the method described in any embodiment of the disclosure when executing the computer program.

An embodiment of the disclosure provides a non-transitory computer storage medium, and the computer storage medium includes at least one executable instruction. Furthermore, the executable instruction is configured to implement the method described in any one embodiment of the disclosure.

Figure 5:
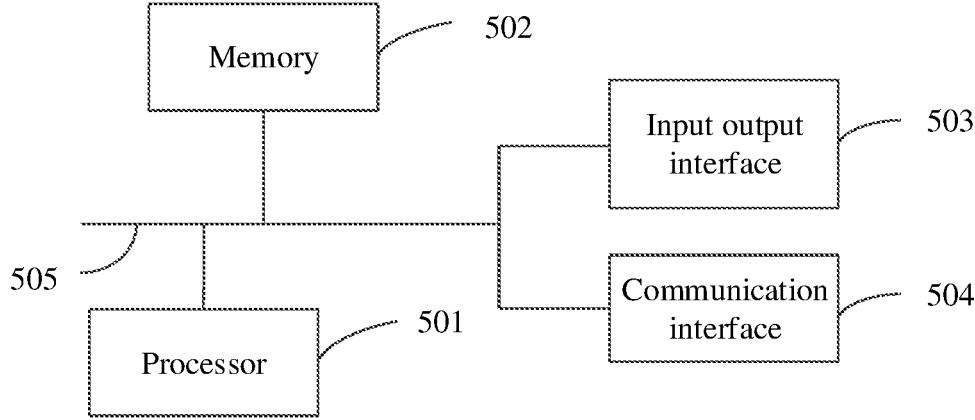
FIG. 5 illustrates a schematic diagram of an electronic device according to an embodiment of the disclosure.

FIG. 5 illustrates a schematic diagram of a hardware structure of the electronic device according to the illustrated embodiment of the disclosure, and the electronic device may include: a processor 501, a memory 502, an input output interface 503, a communication interface 504, and a bus line 505. Furthermore, the processor 501, the memory 502, the input output interface 503, and the communication interface 504 implement a communication connection between each other in the electronic device through the bus line 505.

The processor 501 can be selected from a general central processing unit (CPU), a microprocessor, an application specific integrated circuit (ASIC), or one or more integrated circuits, and is used to execute the computer program to implement the technical solution provided by the method described in the embodiment of the disclosure.

The memory 502 can be selected from a read only memory (ROM), a random-access memory (RAM), a static storage device, a dynamic storage device, etc. The memory 502 can store an operating system and other applications, and therefore, when the technical solution provided by the method described in the embodiment of the disclosure is implemented by using software or hardware, computer program code is stored on the memory 502, and is executable by the processor 501.

The input output interface 503 is configured to connect to an input output module, thereby to implement information input and output. The input output module may be configured as a component in the electric device of the disclosure (not illustrated in the FIGS.) or may be externally connected to a device to provide a corresponding function. An input device can be selected from a keyboard, a mouse, a touch screen, a microphone, various sensors, etc. and an output device can be selected from a display, a speaker, a vibrator, an indicator light, etc.

The communication interface 504 is configured to connect to a communication module (not illustrated in the FIGS.), so as to implement communication interaction between the electric device and other devices. The communication module may implement communication in a wired manner (i.e., a USB, a network cable, etc.), and may also implement communication in a wireless manner (i.e., a mobile network, WIFI, Bluetooth, etc.).

The bus line 505 includes a path that transmits information between various components of the electric device (i.e., the processor 501, the memory 502, the input output interface 503, and the communication interface 504).

It should be noted that although the electric device only illustrates the processor 501, the memory 502, the input output interface 503, the communication interface 504, and the bus line 505. In an illustrated implementation process, the electric device may further include other components necessary for the implementation. In addition, those skilled in the related art can understand that the above-mentioned electric device may also include the components necessary to implement the technical solution of the embodiment of the disclosure, namely, the electric device of the disclosure does not necessarily include all of the components shown in the attached drawings.

It should be understood by those skilled in the related art that the description of any one of the above embodiments is merely exemplary and is not intended to imply that the scope of the disclosure is limited to the above embodiments. Based on the spirit of the disclosure, the technical features in the above embodiments may also be combined and the steps of the disclosure may be implemented in any order. Furthermore, there are many other changes in the different aspects of the disclosure as described above, however, the above-mentioned changes are not provided in detail for brevity.

The disclosure includes all of replacements, modifications, and variations that fall within a broad scope of the embodiments of the disclosure. Therefore, any omission, modification, equivalent replacement, improvement, etc. made within the spirit and principle of the embodiments of the disclosure is included within the protection scope of the disclosure.

What is claimed is:

1. A tumor radiotherapy planning design method, comprising:

obtaining an initial optimization parameter vector set as a current optimization parameter vector set, and calculating a current cost function value;

randomly correcting the current optimization parameter vector set to generate a preset number of alternative optimization parameter vector sets;

performing planning parameter optimization based on the preset number of alternative optimization parameter vector sets, and calculating a total cost function value for each of the preset number of alternative optimization parameter vector sets by a multifunctional optimization total cost function, wherein the multifunctional optimization total cost function is obtained as follows:

$$\mathcal{L}_{tot} = \lambda \cdot \mathcal{L}_{acc} + \mathcal{L}_{qlt}$$

where $\mathcal{L}_{tot}$ represents the multifunctional optimization total cost function, $\mathcal{L}_{acc}$ represents a plan delivery accuracy cost function, $\mathcal{L}_{qlt}$ represents a plan dosimetric quality cost function, $\lambda$ represents a relative weight factor between the plan delivery accuracy cost function and the plan dosimetric quality cost function, and $\lambda$ is in a range of 10.0 to 30.0;

determining current optimal or suboptimal alternative optimization parameter vector sets according to the total cost function values of the preset number of alternative optimization parameter vector sets, sampling to update the current optimization parameter vector set and the current cost function value according to the total cost function values of the current alternative optimization parameter vector sets, and then performing an iteration repeatedly until a convergence condition is satisfied;

outputting an optimal optimization parameter vector set after the iteration, determining planning parameters, and calculating and outputting planning multi-leaf collimator (MLC) leaf positions and dose distributions according to the planning parameters to thereby obtain a tumor radiotherapy plan of a patient, wherein the tumor radiotherapy plan contains the planning MLC leaf positions and the dose distributions; and performing experimental measurement on the tumor radiotherapy plan through a radiation detector array to obtain a measurement result, analyzing a gamma passing rate (GPR) of the measurement result, and performing, when the GPR of the measurement result is greater than or equal to 90%, treatment on the patient based on the tumor radiotherapy plan to facilitate curing the patient.

2. The method as claimed in claim 1, wherein before the obtaining an initial optimization parameter vector set as a current optimization parameter vector set, and calculating a current cost function value, the method comprises:

collecting planning parameters and corresponding GPR data of a plurality of tumor radiotherapy sites, and establishing a training data set; and training a GPR prediction model by using the training data set to obtain a trained GPR prediction model.

3. The method as claimed in claim 1, wherein the performing planning parameter optimization based on the preset number of the alternative optimization parameter vector sets, and calculating a total cost function value for each of the preset number of alternative optimization parameter vector sets, comprises:

performing the planning parameter optimization on the preset number of alternative optimization parameter vector sets to obtain current planning parameters and current dosimetric indicators of each alternative optimization parameter vector set; and calculating the total cost function value for each alternative optimization parameter vector set according to the current planning parameters, the current dosimetric indicators, and objective dosimetric indicators by the multifunctional optimization total cost function.

4. The method as claimed in claim 3, wherein the performing the planning parameter optimization on the preset number of alternative optimization parameter vector sets to obtain current planning parameters and current dosimetric indicators of each alternative optimization parameter vector set, comprises:

performing the following steps for each alternative optimization parameter vector set:

determining beam angles or beam ranges based on computed tomography (CT) images and structures; and performing the planning parameter optimization by a gradient-based optimization algorithm according to the beam angles to obtain the current planning parameters and the current dosimetric indicators, wherein the current dosimetric indicators comprise: homogeneity indices of targets, conformity indices of the targets, and volume doses and average doses of organs at risk.

5. The method claimed in claim 3, wherein the calculating the total cost function value for each alternative optimization parameter vector set according to the current planning parameters, the current dosimetric indicators, and objective dosimetric indicators by a multifunctional optimization total cost function, comprises:

performing the following steps for each alternative optimization parameter vector set:

performing prediction by a trained GPR prediction model according to the current planning parameters to obtain a predicted GPR, and calculating a plan delivery accuracy cost function value by the plan delivery accuracy cost function according to the predicted GPR;

calculating a plan dosimetric quality cost function value according to the current dosimetric indicators and the objective dosimetric indicators by the plan dosimetric quality cost function; and calculating the total cost function value by the multifunctional optimization total cost function according to the plan delivery accuracy cost function value and the plan dosimetric quality cost function value.

6. The method as claimed in claim 1, wherein the sampling to update the current optimization parameter vector set and the current cost function value according to the total cost function values of the current alternative optimization parameter vector sets, and performing an iteration repeatedly until a convergence condition is satisfied, comprises:

performing a sampling decision to determine whether to adopt the current optimal or suboptimal alternative optimization parameter vector sets; and updating the current optimization parameter vector set and the current cost function value using the current optimal or suboptimal alternative optimization parameter vector sets and the corresponding total cost function values respectively, when the current optimal or suboptimal alternative optimization parameter vector sets are adopted; and determining whether the convergence condition is satisfied, wherein the convergence condition comprises: times of the iteration reaching to a preset maximum iteration number, a time of the iteration reaching to a maximum iteration time, and a convergence of cost function value reduction; and returning the step of the randomly correcting the current optimization parameter vector set to generate a preset number of alternative optimization parameter vector sets, when the convergence condition is not satisfied.

7. The method as claimed in claim 6, wherein the performing a sampling decision to determine whether to adopt the current optimal or suboptimal alternative optimization parameter vector sets, comprises:

calculating an acceptance probability of the current optimal or suboptimal alternative optimization parameter vector sets according to the total cost function values of the current optimal or suboptimal alternative optimization parameter vector sets and the current cost function value; and generating a random number between 0 and 1 based on a uniform distribution;

adopting the current optimal or suboptimal alternative optimization parameter vector sets when the random number is less than the acceptance probability; or not adopting the current optimal or suboptimal alternative optimization parameter vector sets when the random number is equal to or greater than the acceptance probability.

8. An electronic device, comprising: a memory, a processor, and a computer program stored on the memory and executable by the processor, wherein the processor is configured to implement the method as claimed in claim 1 when executing the computer program.

9. A non-transitory computer storage medium, comprising: at least one executable instruction, wherein the at least one executable instruction is configured to make a processor to execute the method as claimed in claim 1.

10. The method as claimed in claim 1, wherein the planning parameters comprise beam fluence and aperture shapes.

11. The method as claimed in claim 1, wherein Gaussian distribution is used for the randomly correcting the current optimization parameter vector set.

12. The method as claimed in claim 1, wherein a number of the preset number of alternative optimization parameter vector sets is in a range of 5-20.

13. The method as claimed in claim 1, wherein the initial optimization parameter vector set comprises dose optimization parameter vectors, volume optimization parameter vectors, and weight optimization parameter vectors; the dose optimization parameter vectors comprise dose optimization parameters for all serial organs, the volume optimization parameter vectors comprise volume optimization parameters for all parallel organs, and the weight optimization parameter vectors comprise weight optimization parameters of all targets and organs at risk.

14. The method as claimed in claim 1, wherein the performing, when the GPR of the measurement result is greater than or equal to 90%, treatment on the patient based on the tumor radiotherapy plan to facilitate curing the patient comprises:

in response to the GPR of the measurement result being greater than or equal to 90%, controlling, based on the planning MLC leaf positions in the tumor radiotherapy plan, an MLC to move to shape a radiation beam to irradiate a target tumor site of the patient according to the dose distributions, thereby facilitating curing the patient.

* * * * *